(12) United States Patent
Baetge et al.

(10) Patent No.: US 6,673,603 B2
(45) Date of Patent: Jan. 6, 2004

(54) CELL PASTE COMPRISING KERATINOCYTES AND FIBROBLASTS

(75) Inventors: E. Edward Baetge, St. Sulpice (CH); Thomas Hunziker, Oberhofen (CH); Alain Limat, Trafers (CH); Vincent Ronfard, Lausanne (CH)

(73) Assignee: Modex Therapeutiques, S.A., Lausanna (CH)

( * ) Notice: Subject to any disclaimer, the term of this patent is extended or adjusted under 35 U.S.C. 154(b) by 51 days.

(21) Appl. No.: 09/943,114

(22) Filed: Aug. 30, 2001

(65) Prior Publication Data

US 2002/0048563 A1 Apr. 25, 2002

Related U.S. Application Data

(60) Provisional application No. 60/230,286, filed on Sep. 1, 2000, and provisional application No. 60/299,003, filed on Jun. 18, 2001.

(51) Int. Cl.[7] .............................. C12N 5/00; C12N 5/02; C12N 5/08
(52) U.S. Cl. ........................ 435/325; 435/366; 435/371
(58) Field of Search ................................ 435/368, 384, 435/199, 371, 456, 366, 325, 326; 424/188.1, 93.21, 93.2; 604/890.1; 530/300, 350, 387.3

(56) References Cited

U.S. PATENT DOCUMENTS

| | | | |
|---|---|---|---|
| 5,290,552 A | | 3/1994 | Sierra et al. |
| 5,460,939 A | * | 10/1995 | Hansbrough et al. ......... 435/1.1 |
| 5,902,608 A | | 5/1999 | Read et al. |
| 5,968,546 A | | 10/1999 | Baur et al. |
| 6,010,887 A | | 1/2000 | Bridges et al. ............. 435/91.1 |
| 6,054,122 A | * | 4/2000 | MacPhee et al. ........... 424/94.4 |
| 6,419,920 B1 | * | 7/2002 | Mineau-Hanschke .... 424/93.21 |
| 6,454,811 B1 | * | 9/2002 | Sherwood et al. ........ 623/23.76 |
| 6,497,875 B1 | * | 12/2002 | Sorrell et al. .............. 424/93.7 |
| 2003/0091543 A1 | * | 5/2003 | Klein et al. .............. 424/93.21 |

FOREIGN PATENT DOCUMENTS

| | | |
|---|---|---|
| EP | 0 339 607 | 11/1989 |
| WO | WO 97/06835 | 2/1997 |
| WO | WO 01/24842 | 4/2001 |

OTHER PUBLICATIONS

Nelson and Gay (May 1993) "Effects of UV irradiation on a living skin equivalent." Photochem Photobiol. 57(5):830–7.*

Kuroyanagi et al. (Oct. 1993) "A Cultured Skin Substitute Composed of Fibroblasts and Keratinocytes with a Collagen Matrix: Preliminary Results of Clinical Trials." Ann. Plast. Surg. 31(4): 340–351.*

Maruguchi et al. (Mar. 1994) "A new skin equivalent: keratinocytes proliferated and differentiated on collagen sponge containing fibroblasts." Plast Reconstr Surg. 93(3):537–44.*

Cooper and Hansbrough (Feb. 1991) "Use of a composite skin graft composed of cultured human keratinocytes and fibroblasts and a collagen–CAG matrix to cover full thickness wounds on athymic mice." Surgery 109(2): 198–207.*

Smola et al. (Jul. 1993) "Mutual Induction of Growth Factor Gene Expression by Epidermal–Dermal Cell Interaction." J. Cell. Biol. 122(2): 417–429.*

Meana et al. (1998) "Large surface of cultured human epithelium obtained on a dermal matrix based on live fibroblast–containin fibrin gels." Burns 24: 621–630.*

Ronfard et al. (Dec. 15, 2000) "Long–Term Regeneration of Human Epidermis on Third Degree Burns Transplanted with Autologous Cultured Epithelium Grown on a Fibrin Matrix" Transplantation 70(11): 1588–1598.*

Sirois et al. (1993) "Growth Factors and biological supports for endothelial cell lining: in vitro study." The International Journal of Artificial Organs 16(8): 609–619.*

Davies *Burns* 10: 94–103 (1983).

Hunt and Goodson *Current Surgical Diagnosis & Treatment* pp. 86–98 (1988).

Hunt et al. *The Surgical Wound* Dineen & Hildrick–Smith, eds., pp. 1–18 (1981).

Kannon and Garrett *Dermatol. Surg.* 21: 583–590 (1995).

Riley *Am. Fam. Physician* 24: 107–113 (1981).

Richey et al. *Annals of Plastic Surgery* 23(2): 159–165 (1989).

Winter *Nature* 193: 293–294 (1962).

* cited by examiner

Primary Examiner—Elizabeth Kemmerer
Assistant Examiner—Christopher James Nichols
(74) Attorney, Agent, or Firm—Mintz, Levin, Cohn, Ferris, Glovsky and Popeo, P.C.; Ivor R. Elrifi, Esq.; Christina V. Karnakis, Esq.

(57) ABSTRACT

The present invention provides the use and composition of matter of angiogenic or other growth factors expressed by combining various types and stages of differentiation of allogeneic human cell strains or lines in unencapsulated pastes (mixed with or applied to extracellular matrix material or synthetic biocompatible substances) to be temporarily applied to wounds or defects in the skin or other tissues for the restoration of blood supplying connective tissue to enable organ-specific cells to reestablish organ integrity as well as to inhibit excessive scar formation.

3 Claims, 5 Drawing Sheets

CELL PASTE COMPRISING KERATINOCYTES AND FIBROBLASTS

RELATED APPLICATIONS

This application claims priority to U.S. patent application Ser. No. 60/230,286 "Now Abandoned", filed Sep. 1, 2000 and U.S. patent application Ser. No. 60/299,003 Now Abandoned, filed Jun. 18, 2001, which is herein incorporated by reference in its entirety.

FIELD OF THE INVENTION

The present invention relates generally to tissue regeneration, e.g., the treatment of wounds using a growth factor- or angiogenic factor-secreting cells admixed with a biological or synthetic extracellular matrix and/or attached/applied to a wound dressing or solid nondegradable support matrix.

BACKGROUND OF THE INVENTION

Wounds (i.e., lacerations or openings) in mammalian tissue can result in tissue disruption and coagulation of the microvasculature at the wound face. Repair of such tissue represents an orderly, controlled cellular response to injury. All soft tissue wounds, regardless of size, heal in a similar manner. The mechanisms of tissue growth and repair are biologic systems wherein cellular proliferation and angiogenesis occur in the presence of an oxygen gradient. The sequential morphological and structural changes, which occur during tissue repair have been characterized in great detail and have, in some instances, been quantified. See Hunt, T. K., et al., "Coagulation and macrophage stimulation of angiogenesis and wound healing," in The surgical wound, pp. 1–18, ed. F. Dineen & G. Hildrick-Smith (Lea & Febiger, Philadelphia: 1981).

Tissue regeneration in various organs, such as, e.g., the skin or the heart depends on connective tissue restoring blood supply and enabling residual organ-specific cells such as keratinocytes or muscle cells to reestablish organ integrity. Thus, a relevant function of the mesenchymal cells, i.e., the fibroblasts or, in addition, the endothelial cells of vasculature, is secretion of factors enhancing the healing process, e.g., factors promoting formation of new blood vessels (angioneogenesis) or factors promoting re-epithelialization by proliferating and migrating keratinocytes.

The cellular morphology of a wound consists of three distinct zones. The central avascular wound space is oxygen deficient, acidotic and hypercarbic, and has high lactate levels. Adjacent to the wound space is a gradient zone of local anemia (ischemia), which is populated by dividing fibroblasts. Behind the leading zone is an area of active collagen synthesis characterized by mature fibroblasts and numerous newly formed capillaries (i.e., neovascularization). While new blood vessel growth (angiogenesis) is necessary for the healing of wound tissue, angiogenic agents generally are unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

The primary goal in the treatment of wounds is to achieve wound closure. Open cutaneous wounds represent one major category of wounds. This category includes acute surgical and traumatic, e.g., burn wounds, as well as chronic wounds such as neuropathic ulcers, pressure sores, arterial and venous (stasis) or mixed arterio-venous ulcers, and diabetic ulcers. Open cutaneous wounds routinely heal by a process comprising six major components: i) inflammation, ii) fibroblast proliferation, iii) blood vessel proliferation, iv) connective tissue synthesis, v) epithelialization, and vi) wound contraction. Wound healing is impaired when these components, either individually or as a whole, do not function properly. Numerous factors can affect wound healing, including malnutrition, infection, pharmacological agents (e.g., cytotoxic drugs and corticosteroids), diabetes, and advanced age. See Hunt et al., in Current Surgical Diagnosis & Treatment (Way; Appleton & Lange), pp. 86–98 (1988).

Skin wounds, which do not readily heal can cause the subject considerable physical, emotional, and social distress as well as great financial expense. See e.g., Richey et al., Annals of Plastic Surgery 23(2):159–65 (1989). Indeed, wounds that fail to heal properly finally may require more or less aggressive surgical treatment, e.g., autologous skin grafting. A number of treatment modalities have been developed as scientists' basic understanding of wounds and wound healing mechanisms has progressed.

The most commonly used conventional modality to assist in cutaneous wound healing involves the use of wound dressings. In the 1960s, a major breakthrough in wound care occurred when it was discovered that wound healing with a moist occlusive dressings was, generally speaking, more effective than the use of dry, non-occlusive dressings. See Winter, Nature 193:293–94 (1962). Today, numerous types of dressings are routinely used, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer). See Kannon et al., Dermatol. Surg. 21:583–590 (1995); Davies, Burns 10:94 (1983). Unfortunately, certain types of wounds (e.g., diabetic ulcers, pressure sores) and the wounds of certain subjects (e.g., recipients of exogenous corticosteroids) do not heal in a timely manner (or at all) with the use of such dressings.

Several pharmaceutical modalities have also been utilized in an attempt to improve wound healing. For example, treatment regimens involving zinc sulfate have been utilized by some practitioners. However, the efficacy of these regimens has been primarily attributed to their reversal of the effects of sub-normal serum zinc levels (e.g., decreased host resistance and altered intracellular bactericidal activity). See Riley, Am. Fam. Physician 24:107 (1981). While other vitamin and mineral deficiencies have also been associated with decreased wound healing (e.g, deficiencies of vitamins A, C and D; and calcium, magnesium, copper, and iron), there is no strong evidence that increasing the serum levels of these substances above their normal levels actually enhances wound healing. Thus, except in very limited circumstances, the promotion of wound healing with these agents has met with little success.

What is needed is a safe, effective, and interactive means for enhancing the healing of extensive and/or hard-to-heal wounds that can be used without regard to the type of wound or the nature of the patient population.

SUMMARY OF THE INVENTION

The present invention relates to the use of angiogenic or other growth factors expressed by human cells in unencapsulated pastes (mixed with matrix material or synthetic biocompatible substances) to be temporarily applied to wounds or defects in skin or other tissues for the restoration of blood supplying connective tissue to enable organ-specific cells to reestablish organ integrity as well as to inhibit excessive scar formation.

In one aspect, the invention involves a cell paste for tissue regeneration, e.g., in the treatment of skin wounds containing a cell or a combination of cell types that secrete biologically active substances, admixed with an extracellular matrix material such that the admixture forms a viscous cell paste.

In various embodiments, the cells are stromal, epithelial or organ specific, or a blood-derived cell, such as a fibroblast, a keratinocyte (including outer root sheath cells), a melanocyte, an endothelial cell, a pericyte, a monocyte, a lymphocyte (including plasma cells), a thrombocyte, a mast cell, an adipocyte, a muscle cell, a hepatocyte, a neuron, a nerve or neuroglia cell, an osteocyte, an osteoblast, corneal epithelial cells, chondrocyte, and/or an adult or embryonic stem cell. Preferably, the cells of this invention are allogeneic or xenogenic. Preferably, the cells are differentiated allogenic fibroblasts and keratinocytes.

The main cell type of connective tissue is the fibroblast. Until recently, fibroblasts have been dealt with like homogenous non-differentiating cell populations. However, the fibroblast cell system in various species, including man, is a stem cell system in which the fibroblasts terminally differentiate along seven stages, three containing mitotic and four including post-mitotic cells. See Bayreuther et al., Proc. Natl. Acad. Sci. USA 85:5112–16 (1988); Bayreuther et al., J. Cell. Sci. Suppl. 10:115–30 (1988). In vitro induction of fibroblast differentiation may be performed by chemical or biological agents, such as mitomycin C (Brenneisen et al., Exp. Cell. Res. 211:219–30 (1994)) or growth factors or cytokines (Hakenjos et al., Int. J. Radiat. Biol. 76:503–09 (2000)) such as TGF beta 1, IL-1, IL-6, Interferon alpha. In vitro induction may also be accomplished by irradiation with, e.g., X-rays (Bumann et al., Strahlenther. Onkol. 171:35–41 (1995); UV light (Rodemann et al., Exp. Cell. Res. 180:84–93 (1989); or physical exposure to electromagnetic fields (Thumm et al., Radiat. Environ. Biophys. 38:195–99 (1999). Moreover, induction of differentiation may also be accomplished by culture conditions such as serum starvation or contact inhibition. See Palka et al., Folia Histochem. Cytobiol. 34:121–27 (1996).

To date, the function/biological properties of differentiated fibroblasts have been poorly studied. The pattern of polypeptide expression and secretion, however, varies from mitotic to post-mitotic stages. The respective polypeptides are still being analyzed. See, e.g., Francz, Eur. J. Cell. Biol. 60:337–45 (1993).

In other embodiments, the biologically active molecule is an angiogenic factor or a growth factor, or a combination of at least one angiogenic factor and at least one growth factor. Examples of suitable biologically active molecules include, but are not limited to, epidermal growth factor-growth factor family (EGF); transforming growth factor alpha; HGF/SF; Heparin-binding epidermal growth factor; basic fibroblast growth factor; acidic fibroblast growth factor; other fibroblast growth factors; keratinocyte growth factor; transforming growth factors β1 and β2; transforming growth factor β3; platelet derived growth factor; vascular endothelial growth factor; tumor necrosis factor; interleukin-1 and -6; other interleukin/cytokine family members; insulin-like growth factor I; colony-stimulating factor 1; GM-CSF; and PDGF. Those skilled in the art will recognize that additional biologically active molecules can also be used in the methods and compositions of the invention.

In various embodiments, the extracellular matrix or matrix material can be collagens, alginate, alginate beads, agarose, fibrin, fibrin glue, blood plasma fibrin beads, whole plasma or components thereof, laminins, fibronectins, proteoglycans, HSP, chitosan, heparin, and/or other synthetic polymer scaffolds and solid support materials that could hold or adhere to cells such as wound dressings.

In a further embodiment, the cells are mitotically inactivated, i.e., induced to various stages of differentiation. For example, this inactivation can be accomplished by the administration of mitomycin C or other chemically-based mitotic inhibitors, irradiation with γ-Rays, irradiation with X-Rays, or irradiation with UV light.

In a still further embodiment, the cells are genetically engineered to secrete an exogenous level of angiogenic factors or growth factors. This secretion may be constitutive. Alternatively, this secretion may be controlled by gene switching.

In various other embodiments, the invention also provides methods of treating tissue defects or wounds by administering the cell pastes according to the invention to a wound site on a patient in need of wound treatment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Wound healing is a complex process involving soluble mediators, blood cells, extracellular matrix, and parenchymal cells. Wound healing has three phases - - - the inflammation phase, the tissue formation phase, and the tissue remodeling phase. These phases may overlap in time.

Generally, an injury to tissue disrupts blood vessels and extravasation of blood constituents. Blood clotting helps to reestablish hemostasis and provides a provisional extracellular matrix for cell migration to the wound. At the wound site, platelets (thrombocytes) facilitate the formation of a hemostatic plug and also secrete several mediators of the wound healing process. These mediators include, for example, molecules such as platelet-derived growth factor that attract and activate monocytes and fibroblasts.

Soon after the injury, neutrophils infiltrate the wound and clean the wound of foreign particles and bacteria. The neutrophils are then extruded with the eschar or undergo phagocytosis by macrophages. Monocytes also infiltrate the wound in response to specific chemoattractants, such as fragments of extracellular matrix proteins, transforming growth factors $\beta$, the monocyte chemoattractant protein 1, and become activated macrophages. These activated macrophages release growth factors such as platelet-derived growth factor and vascular endothelial growth factor, which initiate the formation of granulation tissue. Macrophages bind through their integrin receptors to proteins in the extracellular matrix. This binding stimulates macrophage phagocytosis of any microorganisms as well as of fragments of extracellular matrix.

Monocytes, stimulated by adherence to the extracellular matrix, also undergo metamorphosis into inflammatory macrophages. This adherence to the extracellular matrix induces monocytes and macrophages to express colony-stimulating factor 1, tumor necrosis factor $\beta$, and platelet derived growth factor. Other important cytokines expressed by monocytes and macrophages are transforming growth factor $\alpha$, interleukin-1, transforming growth factors $\beta$ 1–3, and insulin-like growth factor I. The monocyte- and macrophage-derived growth factors are thought necessary for the initiation and propagation of new tissue formation in wounds.

Within hours after the injury, reepithelialization of wounds begins. Keratinocytes from the wound edges as well as from residual skin appendages such as hair follicles undergo marked changes in phenotype, including retraction of intracellular tonofilaments, dissolution of most intercellular desmosomes, and formation of peripheral cytoplasmic actin filaments. Furthermore, the hemidesmosomal links between the keratinocytes and the epidermal basement membrane dissolves, which allows the movement of keratinocytes.

Within a couple of days post injury, the keratinocytes at the margin of the wound begin to proliferate behind the migrating cells. As this reepithelialization occurs, the basement-membrane proteins reappear in an ordered sequence from the margin of the wound outward. Keratinocytes then revert to their normal phenotype and attach themselves to the reestablished basement membrane and underlying dermis.

Within about four days post injury, new stroma begins to infiltrate the wound. Concomitantly, macrophages, fibroblasts, and blood vessels also infiltrate the wound. Macrophages provide a source of growth factors that stimulate fibroplasia and angiogenesis. The fibroblasts produce the new extracellular matrix that supports cell in-growth. The new blood vessels carry oxygen and nutrients that sustain the cells.

Growth factors, particularly platelet-derived growth factor and transforming growth factor $\beta 1$, are thought to stimulate fibroblasts of the tissue around the wound to proliferate. In fact, platelet-derived growth factor has been shown to accelerate the healing of chronic pressure sores and diabetic ulcers. Moreover, basic fibroblast growth factor has been used with some success to treat chronic pressure sores.

However, there are many factors that can lead to abnormal wound healing. One example occurs with diabetic ulcers. Typically, diabetic ulcers exhibit multiple biochemical pathologies that can lead to impaired healing. These ulcers happen in patients who cannot sense and relieve cutaneous pressure due to some type of diabetic neuropathy. Frequently, diabetic ulcers become infected because of impaired granulocytic function and chemotaxis. Patients with diabetic ulcers also experience inflammation, impaired neovascularization, decreased synthesis of collagen, increased levels of proteinases, and defective macrophage function.

Overall clinical experience using isolated, e.g., recombinant growth factors and other mediators to accelerate wound healing has not met with great success, perhaps because wound repair is the result of a complex set of interactions between soluble factors, formed blood elements, extracellular matrix, and cells. Combining various growth factors at carefully controlled intervals may promote more effective wound healing.

The present invention provides stromal and epithelial as well as blood-derived cells, including, but not limited to, fibroblasts, keratinocytes including follicular outer root sheath cells, endothelial cells, pericytes, monocytes, lymphocytes including plasma cells, thrombocytes, mast cells, adipocytes, muscle cells, hepatocytes, nerve and neuroglia cells, osteocytes, osteoblasts, corneal epithelial cells, and chondrocytes that are admixed with either a synthetic or natural extracellular matrix ("ECM") to form a cell paste that can be used to improve tissue granulation during wound healing. In one embodiment, the cells may deliver endogenous angiogenic factors or other growth factors. In another embodiment, the cells can be genetically engineered to produce exogenous amounts of the desired factor. Preferably, the cells are allogeneic.

The cells may be either immortalized or primary cell cultures. Cells may be immortalized by any method known to those skilled in the art. A common approach to lengthening the lifespan of a cell is to transfer a virus or a plasmid that contains one or more immortalizing genes. Cell immortalization increases the lifespan of a cell, and the resulting cell line is capable of being passaged many more times than the original cells. Immortalizing genes are well known in the art. See, e.g., Katakura et al., *Methods Cell Biol.* 57:69–91 (1998). Immortalizing proteins or polypeptides include, but are not limited to, the 12S and 13S products of the adenovirus E1A genes, SV40 small and large T antigens, papilloma viruses E6 and E7, the Epstein-Barr Virus (EBV), Epstein-Barr nuclear antigen-2 (EBNA2), human T-cell leukemia virus-l (HTLV-1), HTLV-1 tax, Herpesvirus Saimiri (HVS), mutant p53, and the proteins from oncogenes such as *myc, c-jun, c-ras, c-Ha-ras, h-ras, v-src, c-fgr, myb, c-myc, n-myc,* and *Mdm*2. A preferred immortalization strategy is by transfer of the gene encoding telomerase reverse transcriptase (TERT) into the cell such that TERT was either stably or transiently expressed thereby resulting in the expression of telomerase activity. Telomerase activity, when expressed in normal somatic cells, can lead to elongation of the chromosome tips or protective caps, called telomeres, thereby resulting in the ability of the telomerase expressing cells to become immortalized without becoming transformed (See Jiang, et al., Nature Genetics 21:111–14 (1999) and Morales, et al., Nature Genetics 21:115–18 (1999)).

Telomeres are specialized structures at the ends of eukaryotic chromosomes and appear to function in chromosome stabilization, positioning, and replication. See Blackburn & Szostak, 53 Ann. Rev. Biochem. 163–194 (1984); Zakian, 23 Ann. Rev. Genetics 579–604 (1989); Blackburn, 350 Nature 569–573 (1991). In all vertebrates, telomeres consist of hundreds to thousands of tandem repeats of 5'-TTAGGG-3' sequence and associated proteins. See Blackburn, 350 Nature 569–573 (1991); Moyzis et al., 85 Proc. Natl. Acad. Sci. 6622–6626 (1988). Southern blot analysis of chromosome terminal restriction fragments (TRF) provides the composite lengths of all telomeres in a cell population. See Harley et al., 3445 Nature 458–460 (1990); Allsopp et al., 89 Proc. Natl. Acad. Sci. USA 10114–10118 (1992); Vaziri et al., 52 Am. J. Human Genetics 661–667 (1993). In all normal somatic cells examined to date, TRF analysis has shown that the chromosomes lose about 50–200 nucleotides of telomeric sequence per cell division, consistent with the inability of DNA polymerase to replicate linear DNA to the ends. See Watson, 239 Nature New Biology 197–201 (1972).

This shortening of telomeres has been proposed to be the mitotic clock by which cells count their divisions (see Harley, 256 Mut. Res. 271–282 (1991)), and sufficiently short telomeres may be the signal for replicative senescence in normal cells. See Hastie et al., 346 Nature 866–868 (1990); Lindsey et al., 256 Mut. Res. 4548 (1991); Wright & Shay, 8 Trends Genetics 193–197 (1992). In contrast, the vast majority of immortal cells examined to date show no net loss of telomere length or sequence with cell divisions, suggesting that maintenance of telomeres is required for cells to escape from replicative senescence and proliferate indefinitely. See Counter et al., 11 EMBO 1921–1929 (1992); Counter et al., 91 Proc. Natl. Acad. Sci. USA 2900–2940, 1994).

Telomerase, a unique ribonucleoprotein DNA polymerase, is the only enzyme known to synthesize telomeric DNA at chromosomal ends using as a template a sequence contained within the RNA component of the enzyme. See Greider & Blackburn, 43 Cell 405–413 (1985); Greider & Blackburn, 337 Nature 331–337 (1989); Yu et al., 344 Nature 126–132 (1990); Blackburn, 61 Ann. Rev. Biochem. 113–129 (1992). With regard to human cells and tissues, telomerase activity has been identified in immortal cell lines and in ovarian carcinoma but has not been detected in mortal cell strains or in normal non-germline tissues. See Morin, 59 Cell 521–529, 1989. Together with TRF analysis, these results suggest telomerase activity is directly involved in telomere maintenance, linking this enzyme to cell immortality.

Expression of the human telomerase catalytic component (hTERT) has recently been studied in human somatic cells. See Jiang, et al., 21 Nature Genetics 111–114 (1999). Telomerase expression in normal somatic cells did not appear to induce changes associated with a malignant phenotype such as abnormal growth control or oncogenic transformation. The absence of cancer-associated changes was also reported in human fibroblasts immortalized with telomerase. See Morales, et al., 21 Nature Genetics 115–118 (1999). It was demonstrated that the introduction of telomerase into normal human somatic cells does not lead to growth transformation, does not bypass cell-cycle induced checkpoint controls and does not lead to genomic instability of these cells. Methods for detecting telomerase activity, as well as for identifying compounds or polypeptides that regulate or affect telomerase activity, together with methods for therapy or diagnosis of cellular senescence and immortalization by controlling or measuring telomere length and telomerase activity, have also been described (see PCT International patent application WO 93/23572). The identification of compounds affecting telomerase activity provides important benefits to efforts at treating human disease.

Moreover, the cells according to the invention can be genetically engineered to produce one or more of biologically active molecules such that the molecules are constitutively secreted from the cells. By "constitutively secreted" is meant that the desired biologically active molecule is continuously expressed by the cells or that the gene is continually expressed. Alternatively, the cells can be genetically engineered such that their expression is controlled by gene switching.

As used herein, the terms "gene switch" and "gene switching" refer to methods of regulating gene expression. Specifically, expression of a protein encoded by a gene is controlled by the interaction of certain regulatory proteins, known as DNA-binding proteins, with a region located upstream of the gene. Within the promoter region, there are located several operator regions which contains a specific oligonucleotide sequence to which these DNA-binding proteins specifically bind. These proteins can lead either to activation or repression of gene expression. Thus, they control the regulated expression of genes.

The regulator protein is encoded by a regulatory gene located elsewhere on the chromosome. The interaction of regulator and operator is affected by the presence or absence of particular chemical factors (inducers). Thus, in normal circumstances the regulator is expressed, thereby binding the operator and inhibiting expression of the gene, until a need for the particular protein encoded by the gene is indicated by the appearance in the environment of a specific inducer which interacts with the regulator to inhibit binding to the operator, thus allowing expression of the gene.

For example, an enzyme, which acts upon a sugar molecule is not required unless that sugar is present and, therefore, in the absence of the sugar, the regulatory gene expresses the regulator, which binds the gene operator and inhibits expression of the enzyme. The sugar itself acts as the inducer, which then interacts with the regulator to prevent its binding to the operator thus allowing expression of the enzyme. Digestion of the sugar by the enzyme removes it from the environment allowing the regulator to return to its normal mode and act normally to inactivate enzyme expression.

Such a mechanism can be viewed as a switching arrangement which switches gene expression on and off as dictated by the chemical content of the environment. Gene switching systems of the type described are best known in bacteria and many of the proteins and their target DNA binding sites are known in considerable detail. The regulator proteins usually bind as dimers to operators, which exhibit a two-fold symmetry. The specificity of the regulator/promoter interaction is determined by the sequence specific interaction of specific amino acids of the regulator with the operator DNA. In some systems interactions have been subject to detailed biochemical analysis as well as high resolution X-ray crystallography. The best-characterized class of DNA binding proteins exhibit a common helix-turn-helix motif with some degree of amino acid sequence homology. It is clear that the critical DNA binding domain of the regulator is contained within the helix-turn-helix region.

In eukaryotes it has been shown that control of gene expression is also regulated by the interaction of specific protein factors binding to DNA sequences close to the promoter region of genes. A number of factors have been isolated from yeast and mammalian cells and shown to interact with specific sequence motifs in a sequence-specific manner similar to bacterial systems. Characterization of some of these factors has revealed a new "finger" motif, which may be involved in the sequence specific binding of proteins.

Moreover, it has been demonstrated that eukaryotic gene expression can be controlled through the use of bacterial repressor molecules in eukaryotic cells. In these experiments bacterial operator sequences have been inserted close to the promoters of mammalian genes. Cell lines have been created which express the bacterial repressor. Control of expression of the target eukaryotic genes with operator insertions by repressor molecules has been demonstrated using transient expression assays. In these experiments not only repression of gene expression by the lac repressor has been demonstrated but also induction of gene expression, that is, relief of repression, using IPTG isopropyl thiogalactoside.

Therefore, the detailed knowledge and manipulation of bacterial protein DNA/interactions can be used to control expression in mammalian cell cultures. Gene switching techniques are described, for example in U.S. Pat. No. 6,010,887, which is incorporated herein by reference. Those of ordinary skill in this art will recognize that other methods of gene switch regulation may also be employed.

Although unmodified cells may be used in accordance with the invention, in one preferred embodiment, the isolated cells are genetically engineered. The cells can be genetically engineered to secrete one or more biologically active molecules including, but not limited to, cytokines, growth factors, and/or angiogenic factors, or a combination thereof. Examples of such biologically active molecules are shown in Table 1.

TABLE 1

| Cytokine | Major Source | Target Cells and/or Major Effects |
|---|---|---|
| Epidermal growth factor (EGF) | Platelets | Pleiotropic-cell motility and proliferation |
| Transforming growth factor "alpha" (TGFα) | Macrophages, epidermal cells | Pleiotropic-cell motility and proliferation |
| Heparin-binding epidermal | Macrophages | Pleiotropic-cell motility and proliferation |
| Basic fibroblast growth factor | Macrophages, endothelial cells | Angiogenesis and fibroblast proliferation |
| Acidic fibroblast growth factor | Macrophages, endothelial cells | Angiogenesis and fibroblast proliferation |
| Keritinocyte growth factor | Fibroblast | Epidermal-cell motility and proliferation |
| Transforming growth factor β family (TGFβ) | | Fibrosis and increased tensile strength |

TABLE 1-continued

| Cytokine | Major Source | Target Cells and/or Major Effects |
|---|---|---|
| Transforming growth factors β1 and β2 (TGFβ1 & TGFβ2) | Platelets, macrophages | Epidermal-cell motility, chemotaxis of macrophages and fibroblasts, extracellular matrix synthesis and remodeling |
| Transforming growth factor β3 (TGF β3) | Macrophages | Antiscarring effects |
| Platelet derived growth factor (PDGF) | Platelets, macrophages, epidermal cells | Fibroblast proliferation and chemoattraction, macrophage chemoattraction and activation |
| Vascular endothelial growth factor | Epidermal cells, macrophages; endothelial cells | Angiogenesis and increased vascular permeability |
| VEGF A | Blood vessel endothelial cells | Endothelial cell migration and blood vessel formation |
| VEGF B | Blood vessel endothelial cells | Endothelial cell migration and blood vessel formation |
| VEGF C | Lymphatic vessel endothelial cells | Endothelial cell migration and lymphatic vessel formation |
| VEGF D | Lymphatic vessel endothelial cells | Endothelial cell migration and lymphatic vessel formation |
| Tumor necrosis factor "alpha" (TNFα) | Neutrophils | Pleiotropic expression of growth factors |
| Interleukin-1 (IL-1) | Neutrophils | Pleiotropic expression of growth factors |
| Insulin-like growth factor I | Fibroblasts, epidermal cells | Reepithelialization and granulation-tissue formation. |
| Colony-stimulating factor 1 (CSF-1) | Multiple cells | Macrophage activation and granulation tissue formation. |
| Granulocyte Macrophage colony stimulating factor (GM-CSF) | Multiple cells | Macrophage activation and granulation tissue formation |

Column 1 of Table 1 names suitable biologically active molecules. Column 2 displays the major source of the particular biologically active molecule. Finally, Column 3 shows the target cells and/or major effect of the given biologically active molecule.

Control of the delivery of the secreted biologically active molecule can be achieved by any method known to those skilled in the art. For example, the expression of multiple gene products may be controlled by a single promoter system. Alternatively, the expression of multiple gene products may be controlled by multiple promoter systems, with each promoter system regulated either constitutively, by gene switching or by some combination of both. Further, control over the secretion of a particular biologically active molecule may be accomplished by up-regulating the wild-type factor.

A number of well-known methods exist for introducing genetic material into target cells. These include the use of polycations such as DEAE-dextran (see McCutchan, et al., J. Natl. Cancer Inst. 41:351–57 (1968) and Kawai et al., Mol. Cell. Biol. 4:1172–74 (1984)); calcium phosphate coprecipitation (see Graham et al., Virology 52:456–67 (1973)); electroporation (see Neumann et al, EMBO J. 7:841–45 (1982)); lipofection (see Felgner et al., Proc. Natl. Acad. Sci. USA 84:7413–17 (1987)); retrovirus vectors (see Cepko et al., Cell 37:1053–62 (1984)); and microinjection (see Capecchi et al., Cell 22:479–88 (1980)).

Moreover, one skilled in the art will recognize that any other method suitable for delivering an exogenous biologically active molecule into the cells may also be employed.

Using any of the above-mentioned transfection methods, control over the secretion of a variety of biologically active molecules may be achieved by admixing any number of cell types secreting the various biologically active molecules.

Additionally, the cells of the present invention may also be either mitotically active or inactive. By "mitotically active" is meant that the cells actively undergo mitosis. Conversely, by "mitotically inactive" is meant that the cells do not actively undergo mitosis. Mitotically inactive cells may be growth arrested by any means known in the art. By way of non-limiting example, the cells may be growth arrested by chemical means, such as, for example, by the administration of mitomycin C. Additionally, the cells may be growth arrested by exposure to UV light, X-Ray, or gamma radiation. It is important to note that, e.g. mitotically inactivated, human fibroblast cells terminally differentiate and thereby change the pattern of polypeptide expression and secretion (Francz, Eur. J. Cell. Biol. 60:337–45 (1993)). As a further example, keratinocyte differentiation usually depends on culture conditions (composition of culture media, $Ca^{2+}$-concentration, air-exposed=lifted culture), but may also be induced to differentiate, e.g., by mitomycin C.

The cells according to the invention may either be autologous, allogeneic, or xenogeneic. Most preferably, the cells of the present invention are allogeneic.

Xenogeneic cells can be isolated for example from transgenic animals expressing molecules of interest.

Stromal cells comprising, for example, fibroblasts, can be isolated by any method known to those skilled in the art. For example, fibroblasts may be derived from organs, such as skin, liver, and pancreas. These organs can be obtained by biopsy (where appropriate) or upon autopsy. Specifically, sufficient quantities of fibroblasts can be obtained rather conveniently from any appropriate cadaver organ.

Fibroblasts can be readily isolated by disaggregating an appropriate source organ or tissue. By "source organ or tissue" is meant the organ or tissue from which the cells are obtained. Disaggregation may be readily accomplished using techniques known to those skilled in the art. Examples of such techniques include, but are not limited to mechanical disaggregation and/or treatment with digestive enzymes and/or chelating agents that weaken the connections between neighboring cells thereby making it possible to disperse the tissue into a suspension of individual cells without appreciable cell breakage. Specifically, enzymatic dissociation can be accomplished by mincing the tissue and treating the minced tissue with any of a number of digestive enzymes, either alone or in combination. Suitable enzymes include, but are not limited to, trypsin, chymotrypsin, collagenase, elastase, hyaluronidase, Dnase, pronase, and/or dispase. Mechanical disruption can be accomplished by a number of methods including, but not limited to, the use of grinders, blenders, sieves, homogenizers, pressure cells, or insonators. See Freshney, Culture of Animal Cells. A Manual of Basic Technique, 2d Ed., A.R. Liss, Inc., New York, 1987, Ch. 9, pp. 107–26.

Once the source tissue has been reduced to a suspension of individual cells, the suspension should be fractionated into subpopulations from which the fibroblasts and/or other stromal cells and/or elements can be recovered. Fractionation may be accomplished using standard techniques for cells separation including, but not limited to, cloning and selection of specific cells types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter-current distribution, electrophoresis and fluorescense-activated cell sorting. See Freshney, Culture of Animal Cells. A Manual of Basic Techniques, 2d Ed., A.R. Liss, Inc., New York, 1987, Ch. 11 and 12, pp. 137–68. Those skilled in the art will recognize that other suitable cell fractionation technique(s) can also be used.

Preferably, the isolation of fibroblasts is accomplished by explantation of skin pieces according to the method of Sly and Grubb. See Sly et al., Methods Enzymol. 58:444–50 (1979).

To create the cell paste according to the invention, the cell strains or genetically engineered cell lines are preferably mixed with a supporting biological or synthetic extracellular matrix or matrix material (ECM). One skilled in the art will recognize that the term "ECM" refers to the noncellular material distributed throughout the body of multicellular organisms. It is comprised of diverse constituents such as glycoproteins, proteoglycans, complex carbohydrates, and other molecules. Major functions of the ECM include, but are not limited to, providing structural support, tensile strength or cushioning; providing substrates and pathways for cell adhesion and cell migration; and regulating cellular differentiation and metabolic function. ECM proteins include, for example, collagens, elastin, fibronectin, laminin, proteoglycans, vitronectin, thrombospondin, tenascin (cytoactin), entactin (nidogen), osteonectin (SPARC), anchorin CII, chondronectin, link protein, osteocalcin, bone sialoprotein, osteopontin, epinectin, hyaluronectin, amyloid P component, fibrillin, merosin, s-laminin, undulin, epilligrin, and kalinin. Preferred ECM proteins for use according to this invention include collagen, alginate, agarose, fibrin, fibrin glue, laminins, fibronectins, HSP, chitosan, heparin and/or other synthetic polymer scaffolds.

Cell density and the concentration of the extracellular matrix may be varied for the desired clinical application. For example, certain wounds may require greater or lesser cell densities and/or different consistency pastes. Determination of the appropriate cell density and concentration of ECM is within the routine skill of those in the art. The cell suspension can come from one cell type or can be comprised of a mixture of different cell types. For example, the cell mixture may include 50% of keratinocytes and 50% of fibroblasts. Moreover, the suspension may be comprised of more than two different cell types. The percentages of each cell type may vary depending on the intended use. The cells can also be pre-induced or co-cultured in vitro in order to optimize the healing response on the wound. For example, fibroblasts can be pre-incubated with TGF-beta (from 0.1 to 30 ng/ml of medium) for 1 to 21 days prior to wound application.

In one preferred embodiment, the invention involves a human allogeneic fibroblast cell line admixed with ECM materials to form a viscous paste to adhere to a wound. In this embodiment, this cell line is preferably not genetically engineered. This cell line may be mitotically inactivated by any means known to those skilled in the art. Preferably, the paste is both biodegradable and biocompatible. The paste may be applied to the wound as need, for example, once weekly. Application of the cell paste according to this embodiment facilitates the induction of granulation tissue and the stimulation of wound closure. As previously described, immortalized fibroblast and keratinocyte cell lines would also be preferred embodiments. The preferred immortalization method would be through directly adding the gene for TERT into the primary human keratinocyte and fibroblast cells such that the TERT gene is constitutively expressed. In addition, a transient immortalization using a protein domain transport sequence (TAT, VP22, MTS, etc. attached to the TERT protein might be more preferable in that the gene is not permanently inserted into the immortalized cell but is instead added as a fusion protein to the growth medium. In this way, the cell line could be continuously expanded, banked, and screened for stable properties (growth rate, factor secretion, etc.), without the continual need for the revalidation of new primary cell sources. The cell lines immortalized in this way would preferentially be mitotically inactivated (as described below) before application to the wound or tissue repair site as a paste, biological matrix mixture, or as attached or adsorbed to a wound dressing.

The present invention has human clinical and veterinary applications. The cell paste of the invention can be used to treat humans and non-human animals, including, a non-human primate, mouse, rat, dog, cat, pig, sheep, cow, or horse. The cell paste according to the invention can be used for tissue regeneration such as, e.g., in skin wound treatment or in treatment of parodontitis.

For example, the cell paste of the invention can be incorporated into other pharmaceutical compositions suitable for administration. Such compositions can comprise the cell paste and an additional acceptable carrier. As used herein, "biologically acceptable carrier" is intended to include any and all solvents, dispersion media, coatings, antibacterial and antifungal agents, isotonic and absorption delaying agents, and the like, compatible with biologics administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions can be included in a container, pack, or dispenser together with instructions for administration.

The dosage regimen is selected in accordance with a variety of factors including species, age, weight, sex, and medical condition of the patient; type and severity of the condition to be treated; the route of administration; and the particular cells employed. An ordinarily skilled physician or veterinarian can readily determine and prescribe the effective amount required to prevent, counter or arrest the progress of the condition.

The invention will be further described in the following examples, which do not limit the scope of the invention described in the claims.

EXAMPLE 1: Isolation of Fibroblasts

The isolation of fibroblasts may be carried out as follows: fresh tissue samples are thoroughly washed and minced in Hank's balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, and serially cultured or stored frozen in liquid nitrogen (see, Naughton et al., 1987, J. Med. 18(3&4):219–250). Fibroblasts or subpopulations of fibroblasts such as dermal papilla cells or myofibroblasts can be isolated from explant outgrowth culture. Once isolated, the stromal cells are ready for admixture with the ECM paste.

EXAMPLE 2: Testing the Effective Dose of Mitomycin C

Previous work had shown the efficient concentrations of mitomycin C (MMC) for growth-arrest of mouse 3T3 cells is 2 $\mu$g/ml (Rheinwald and Green, Cell 6:331–43 (1975)) and for human dermal fibroblasts 8 $\mu$g/ml (Limat et al., J. Invest. Dermatol. 92:758–62 (1989)).

Both normal (CRL 1213) and FGF1-transfected rat fibroblasts (175-CRL) as well as normal human fibroblasts (MDX12 and EDX 1) were growth arrested using the following method. The fibroblasts were grown in DMEM+ 10% FCS, 25 mM Hepes, 1 mM pyruvate, 2 mM L-Gln, 100 U/ml penicillin, 100 $\mu$g/ml streptomycin in T75 flasks. At confluency, the cells were detached and plated at a density of $10^5$ cells/cm$^2$, further incubated for 48 h, then treated with mitomycin C (MMC) at 0, 2, 4, 8, 12 $\mu$g/ml for 5 h. The cells were then rinsed with PBS and detached with 0.05% trypsin/0.02% EDTA. The remaining cells were plated at densities of 100 to 5000 cells/cm$^2$ in T25-flasks respectively (10 flasks for each density). These cells were incubated at 37° C. with 2 media changes per week.

Growth arrest efficiency of the cells was measured by cell counting in a hemacytometer at weekly intervals in the flasks plated at a density of 5000 cells/cm$^2$ and inspection of appearing colonies in the flasks plated at a density of 100 cells/cm$^2$. Changes in cell morphology were also examined. For the human primary fibroblasts EDX 1 and hTERT immortalized human fibroblast line MDX12, a concentration of 8 $\mu$g/ml MMC was appropriate, in agreement with previous data (Limat et al., J. Invest. Dermatol. 92:758–62 (1989)). For the rat fibroblast line CRL 123, MMC-concentrations above 4 $\mu$g/ml were toxic, while 2 $\mu$g/ml MMC proved to be optimal. For the rat fibroblast cell line 175-CRL transfected with the FGF1-gene, cell growth was efficiently arrested at a concentration of 1 $\mu$g/ml MMC. Concentrations below 1 $\mu$g/ml were not necessarily efficacious and higher concentrations were progressively toxic. In mitomycin C-treated fibroblasts (with the appropriate mitomycin-C dose) recovered from cryogenic storage, the cell recovery was 50% (in agreement with Limat et al., In Vitro Cell Dev. Biol. 26:709–12 (1990)).

EXAMPLE 3: Testing of Optimal Dilution of TissuCol (fibrin glue) and Standard Human Plasma Once the growth arrest efficiency was established, the range of optimal dilutions of TissuCol was determined. TissuCol was diluted with PBS without Ca$^{2+}$/Mg$^{2+}$ or directly with culture medium in a ratio of 1:5, 1:10 and 1:20. The TissuCol was then cast in 12-multiwell dishes (surface= 3.8 cm$^2$; 0.25, 0.5, 1 ml per well), the pastes overlaid with 1 ml culture medium after 30 min., and the state of the pastes followed during several days. Also, the maniability/handling of the pastes was checked using manual manipulation methods. Optimal dilutions of the TissuCol was determined to be in a range between 1:2 and 1:40. Normal human plasma can also be used as a matrix material for the production of clotted cell pastes in the wound site. Mixtures made from normal human plasma and calcic thrombin (1–500 U/ml) resulting in from 50–100% final plasma concentration, result in the formation of fibrin clotted material of sufficient maniability and handling characteristics to be able to substitute for commercially available fibrin glues such as Baxter's Tissucol and Haemacure's APR concentrated fibrin-based products.

EXAMPLE 4: Testing of the Optimal Cell Density Within the Fibrin Paste

After establishing the growth arrest efficiency and optimal TissuCol concentrations, the optimal cell density within the TissuCol was determined. Rat and human MDX12 as well as EDX1 fibroblasts were mixed at selected densities ($10^3$–$10^5$ cells per ml) with the selected dilution of TissuCol and poured into wells of 12-multiwell dishes. Both mitotically active and mitotically inactivated fibroblasts were used. The behavior of the fibrin pastes was followed by, (a) phase contrast optic visualization, (b) viability testing (Trypan blue) and cell counts at selected intervals following solubilization of the fibrin paste by plasmin or trypsin, (c) re-plating of the fibroblasts harvested from the solubilized fibrin pastes in culture dishes. Operative densities of fibroblasts inside the fibrin pastes was determined by macroscopic visualization of the state of the pastes to be between the range of $10^3$ and $5\times10^6$. In the absence of antiproteases (e.g. Trasylol®, aprotinin) in the culture medium, the pastes were rapidly digested when they contained mitotic fibroblasts. In the presence of postmitotic fibroblasts, the digestion process was not apparent.

EXAMPLE 5: In vivo testing of the cell paste

The in vivo model of acute wound healing was performed according to Raffoul et al. Eur. J. Plast. Surg. (1993) 16:180–85. After several days of acclimatization, a square-shaped excision of 3 cm in length (corresponding to 9 $cm^2$) was made from the back skin. Five rats for each of the experimental groups below were tested by applying the indicated cell paste. The wounds were left uncovered following the application.

Acute wound healing experiments were conducted on the back of hairless rats. The following groups were tested:

1. TissuCol alone (control)
2. TissuCol+rat CRL fibroblasts (postmitotic)
3. TissuCol+human primary EDX 1 fibroblasts (postmitotic)

Five rats were used per experimental group. The progression of the healing process was determined by wound appearance and measuring daily the wound surface and comparing % closure versus the initial wound size. Digital photographs of the wounds were also taken. The experiment was terminated when the first group of rats had healed completely. The wound was then excised and the material processed for conventional histology. The histological analysis examined differences in thickness of the granulation tissue, e.g. cellularity, vascularization and re-epithelialisation. A major endpoint for evaluation was the amount of granulation tissue evaluated using conventional histology. All three conditions resulted in the formation of granulation tissue and healed wounds without evidence of any adverse events.

EXAMPLE 6: Growth Factor Production in Co-Cultures of Differentiated Fibroblasts and Keratinocytes Suspended in TissuCol In Vitro The goal of the present study was to demonstrate that postmitotic human fibroblasts, postmitotic keratinocytes, or the combination of both, secrete growth factors when embedded in fibrin (TissuCol - - - Baxter).

Human fibroblasts (passage 8 to 12) were recovered from the cryogenic storage, washed in culture medium (DMEM with 10 % fetal calf serum), plated in 15 ml culture medium per T75 flask and cultured until they reached 80% of cellular confluency. Then the cells were rendered post mitotic by treatment with 8 $\mu$g/ml of mitomycin C (Sigma, MMC) during 5 hours. Human keratinocytes recovered from frozen vials were plated in T25 flasks in KGM.(Clonetics Corp.) or Keratinocyte Defined SFM (Life Technologies).

Keratinocytes were prepared in two different ways: (1) preconfluent keratinocytes: keratinocytes were grown in culture medium as previously defined until reaching a confluency of 80%. Then, the cells were rendered post mitotic by treatment with MMC (see above), (2) post-confluent keratinocytes: were grown in culture medium for 3 days in the post-confluent state. Then, the cells were rendered post mitotic by treatment with MMC (see above). After the mitomycin C treatment, cells were washed and trypsinized producing a cell single cell suspension. A concentration of $2\times10^6$ cells/ml was mixed within the fibrinogen solution. To prepare the fibrin paste, both syringes containing the fibrinogen and the thrombin (1–500 U/ml) were allowed to thaw at RT. The fibrinogen (1 ml) was transferred directly into a 15 ml tube containing 1 ml PBS without Ca/Mg (kept at 4° C.), then further diluted with 6 ml PBS w Ca/Mg, representing at this point a dilution of 1:8. The thrombin (1 ml) was diluted with PBS w Ca/Mg (1:5).

Post-mitotic fibroblasts or keratinocytes were detached with trypsin from the culture dishes. To prepare a paste in a well of a 12-multiwell dish, 0.2 ml of a cell suspension containing $5\times10^6$ cells/ml was pipetted and 0.05 ml of diluted thrombin (1:5) was added to the cell suspension. Finally, 0.25 ml fibrinogen diluted 1:8 were pipetted into each well and the plates gently agitated. After 10 min, the paste was solidified, and 1 ml of medium was added onto the pastes.

Media used were: (1) DMEM+2% human AB serum (PAA); (2) KDM (BioWhittaker) w/o BPE, FGF2.After 3 days of culture, media supernatants were harvested and the pastes were frozen at −80° C. To evaluate growth factors secreted by the cells: the supernatants from harvested media or from extracted paste were thawed and analyzed using ELISA method (R&D systems): FGF2, FGF7, VEGF, TGF-beta, GM-CSF.

Figure 1:
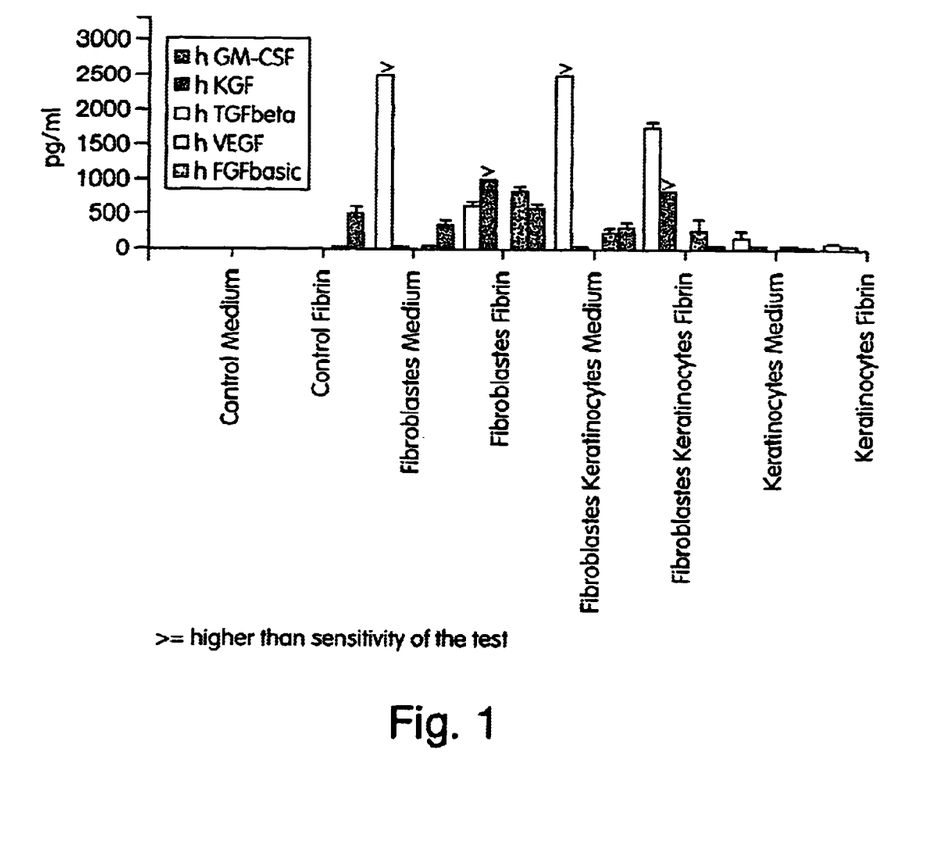
FIG. 1 is a histogram showing the results of secretion of growth factors from the cell/fibrin paste mixture.
Figure 2:
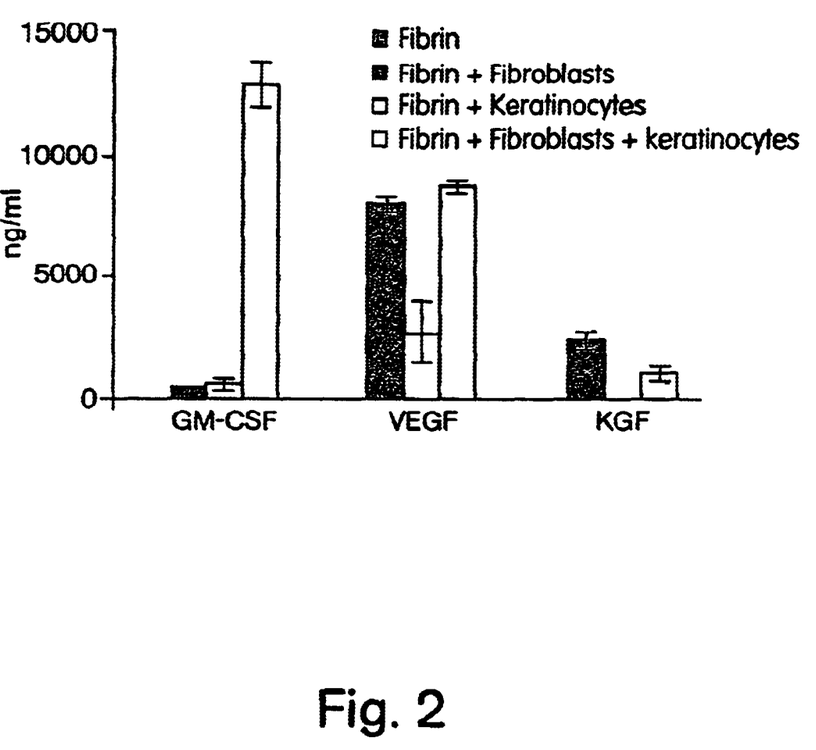
FIG. 2 is a histogram showing the secretion of keratinocyte growth factor (KGF), vascular endothelial growth factor (VEGF), granulocyte-macrophage colony-stimulating factor (GM-CSF) from cultures containing keratinocytes alone, fibroblasts alone, or co-cultured keratinocytes and fibroblasts in a fibrin paste. Medium was analyzed for cytokine contends after 3 days of culture. Total cell number was identical for each condition.

The results demonstrating the secretion of growth factors from the cell/fibrin paste mixture are shown in FIG. 1.

Figure 3:
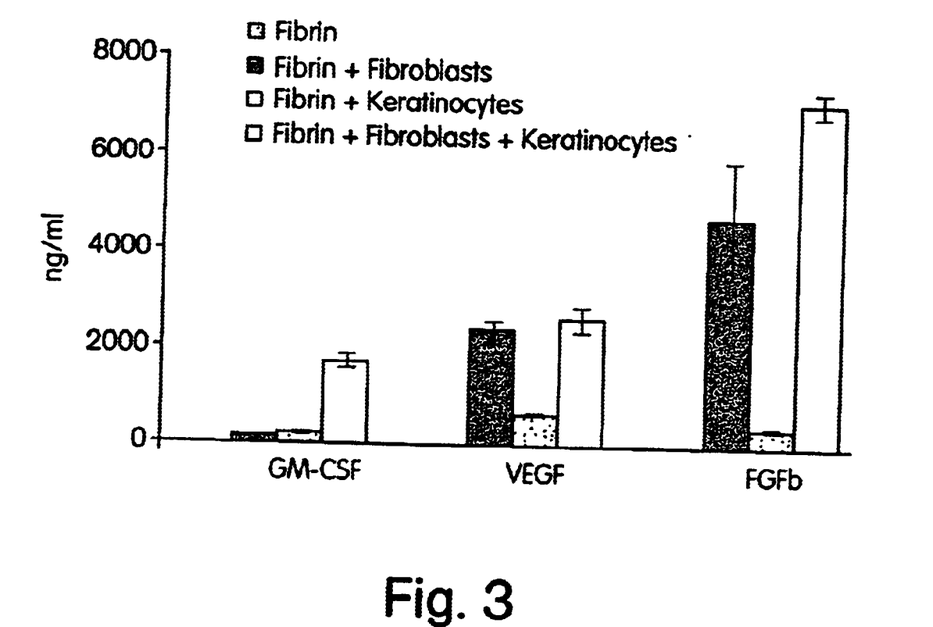
FIG. 3 is a histogram showing the secretion of basic fibroblast growth factor (bFGF), vascular endothelial growth (VEGF), granulocye-macrophage colony-stimulating factor (GM-CSF) from cultures containing keratinocytes alone, fibroblast alone or co-cultured keratinocytes and fibroblasts in a fibrin paste. Cellular and fibrin extracts were analyzed for cytokine contents after 3 days of culture. Total cell number was identical for each condition.

Cells were grown within the fibrin paste as described previously. After 3 days of culture the supernatant and the fibrin paste extract were evaluated for growth factor production. Control medium and fibrin without cells did not contain any growth factors. Fibroblasts alone mainly secreted KGF and VEGF in the medium, in addition bFGF was present in large quantity in the fibrin paste extract (1000 pg/ml/$10^6$ cells). Keratinocytes alone secreted mainly GM-CSF in the medium. The combination of fibroblasts and keratinocytes secreted growth factors produced separately by each cell type usually in higher amounts. A synergistic effect was observed for the secretion of GM-CSF in the medium as shown in FIG. 3 and in the extracts of the cells and fibrin paste as shown in FIG. 4.

Figure 4:
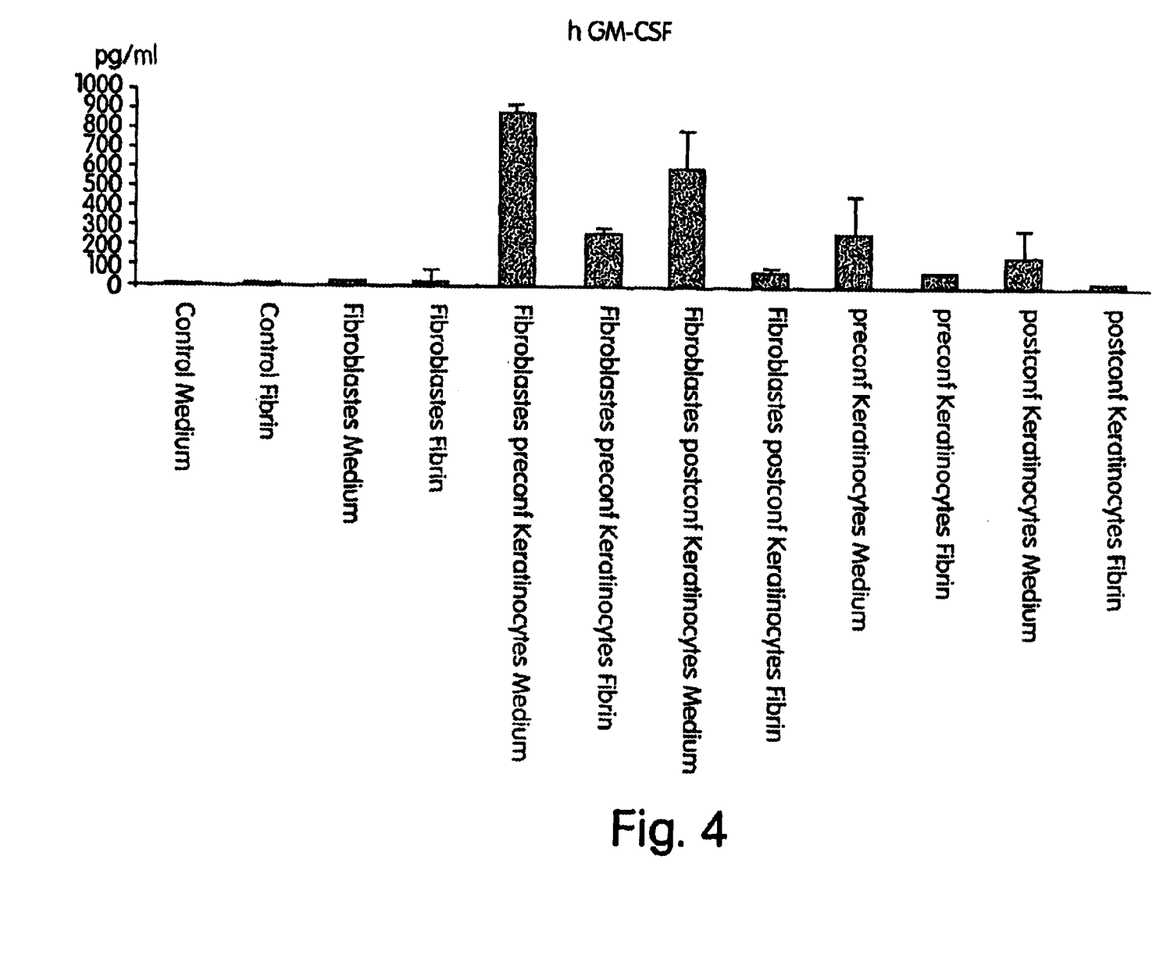
FIG. 4 is a histogram showing the effect of keratinocyte confluency on the secretion of GM-CSF.

The effect of keratinocyte confluency on the secretion of GM-CSF is shown in FIG. 4.

Keratinocytes were grown in culture dishes as previously described. They were harvested at two different stages of the culture; (1) pre-confluency (preconf) before the cells completely covered the bottom of the dish (2) post-confluency (postconf) 3 days after the cells have covered the bottom of the culture dish. The suspension of keratinocytes obtained from these 2 cultures was then included in the fibrin paste and grown for 3 days. Medium and paste was analyzed as described above. Results show that higher levels of GM-CSF are secreted when keratinocytes are harvested before they have reached confluency.

Figure 5:
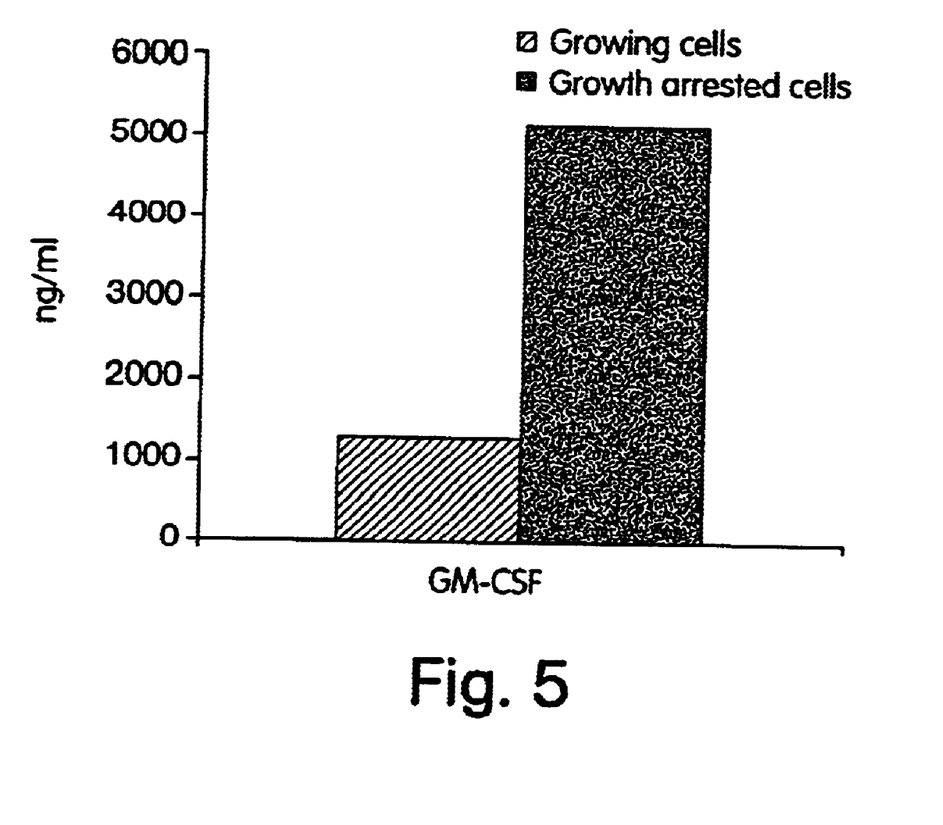
FIG. 5 is a histogram showing the secretion of granulocyte-macrophage colony-stimulating factor (GM-CSF) from cultures containing co-cultured keratinocytes and fibroblasts in a fibrin paste. The cells were either non-treated with Mitomycin C (growing cells) or treated with Mitomycin C (growth arrested cells). Cell supernatants were analyzed for cytokine contents after 3 days of culture. Results are expressed in ng of GM-CSF/ml of medium.

Finally, in one embodiment of the invention, the ability of keratinocytes and fibroblasts made postmitotic by growth arrest in Mitomycin C can lead to further differentiation of the cells. Such growth arrested differentiation can lead to increased secretion of growth factors and cytokines as demonstrated in FIG. 5.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A cell paste, comprising:

a) one or more keratinocytes and fibroblasts that naturally secretes on or more biologically active molecules selected from the group consisting of GM-CSF, V GF, KGF, bFGF, TGFfβ admixed with b) an extracellular matrix or matrix material, wherein said extracellular matrix or matrix material is selected from the group consisting of collagens, alginate, alginate beads, agarose, fibrin, fibrin glue, blood plasma, fibrin beads, laminins, proteoglycans, fibronectins, chitosan, and heparin, c) wherein the cells are mitotically inactivated by irradiation, and;

d) wherein the cells are allogeneic such that the resulting admixture forms a viscous cell paste.

2. The cell paste of claim 1 wherein the one or more keratinocytes and fibroblasts are differentiated fibroblasts and keratinocytes.

3. The cell paste of claim 1 wherein the cells are immortalized using at least one gene or polypeptide selected from the group consisting of the 12S and 13S products of the adenovirus EJA genes, hTERT, SV40 small T antigen, SV40 large T antigen, papilloma viruses E6 and B7, the Epstein-Barr Virus (EBV), Epstein-Barr nuclear antigen-2 (EBNA2), human T-cell leukemia virus-l (HTLV-l), HTLV-l tax, Herpesvirus saimiri (HVS), mutant p53, *myc, c-jun, c-ras, c-Ha-ras, h-ras, v-src, c-fgr, myb, c-myc, n-myc,* and *Mdm*2.

* * * * *

UNITED STATES PATENT AND TRADEMARK OFFICE
CERTIFICATE OF CORRECTION

PATENT NO. : 6,673,603 B2
APPLICATION NO. : 09/943114
DATED : January 6, 2004
INVENTOR(S) : E. Edward Baetge et al.

It is certified that error appears in the above-identified patent and that said Letters Patent is hereby corrected as shown below:

In claim 1, column 18, line 1, delete "V GF" and insert --VEGF-- therefor.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,673,603 B2 | Page 1 of 1 |
| APPLICATION NO. | : 09/943114 | |
| DATED | : January 6, 2004 | |
| INVENTOR(S) | : E. Edward Baetge et al. | |

It is certified that error appears in the above-identified patent and that said Letters Patent is hereby corrected as shown below:

In claim 1, column 18, line 2, delete "TGFfβ" and insert --TGFβ-- therefor.

Signed and Sealed this
Seventh Day of August, 2012

David J. Kappos
*Director of the United States Patent and Trademark Office*